United States Patent
Fournel et al.

(10) Patent No.: US 8,457,863 B2
(45) Date of Patent: Jun. 4, 2013

(54) METHOD OF ADJUSTING INJECTION, COMBUSTION AND/OR POST-TREATMENT PARAMETERS OF AN INTERNAL COMBUSTION ENGINE WITH AUTO-IGNITION

(75) Inventors: Johan Fournel, Robion (FR); Alain Lunati, La Fare les Oliviers (FR)

(73) Assignee: SP3H, Aix En Provence (FR)

( * ) Notice: Subject to any disclaimer, the term of this patent is extended or adjusted under 35 U.S.C. 154(b) by 534 days.

(21) Appl. No.: 12/598,579

(22) PCT Filed: May 7, 2008

(86) PCT No.: PCT/FR2008/000645
§ 371 (c)(1),
(2), (4) Date: Mar. 3, 2010

(87) PCT Pub. No.: WO2008/152239
PCT Pub. Date: Dec. 18, 2008

(65) Prior Publication Data
US 2010/0168984 A1    Jul. 1, 2010

(30) Foreign Application Priority Data
May 7, 2007 (FR) ...................................... 07 54908

(51) Int. Cl.
*F02M 51/00* (2006.01)
*F02M 51/04* (2006.01)

(52) U.S. Cl.
USPC ............................................ 701/103; 123/494

(58) Field of Classification Search
USPC .......... 701/103, 101, 102, 114, 115; 123/575, 123/1 A, 494; 250/339.6, 339.12, 341.6
See application file for complete search history.

(56) References Cited

U.S. PATENT DOCUMENTS

| | | | |
|---|---|---|---|
| 5,262,645 A * | 11/1993 | Lambert et al. | 250/339.04 |
| 5,347,475 A | 9/1994 | Taylor et al. | |
| 2003/0179002 A1 * | 9/2003 | Beylich et al. | 324/663 |
| 2008/0162016 A1 * | 7/2008 | Lunati et al. | 701/103 |

FOREIGN PATENT DOCUMENTS

| | | |
|---|---|---|
| DE | 10252476 A1 | 5/2004 |
| EP | 1306537 A2 | 5/2003 |
| EP | 1757791 A2 | 2/2007 |
| EP | 1854982 A1 | 11/2007 |

* cited by examiner

Primary Examiner — Mahmoud Gimie
(74) Attorney, Agent, or Firm — Arent Fox LLP

(57) ABSTRACT

The invention relates to a method for adjusting injection, combustion and/or post-treatment parameters of an internal combustion engine with auto-ignition, characterized in that it comprises a step of determining the content and the type of biofuel present in the fuel feeding the injection system. The invention also relates to a motorization system and equipment for implementing this method, implementing a sensor for determining the content and the type of biofuel present in the fuel feeding the injection system.

16 Claims, 2 Drawing Sheets

METHOD OF ADJUSTING INJECTION, COMBUSTION AND/OR POST-TREATMENT PARAMETERS OF AN INTERNAL COMBUSTION ENGINE WITH AUTO-IGNITION

CROSS-REFERENCE TO RELATED APPLICATION

This application is a National Stage entry of International Application No. PCT/FR2008/000645, filed May 7, 2008, which claims priority of French Application No. 0754908, filed May 7, 2007. The disclosure of the prior application is hereby incorporated in its entirety by reference.

The invention relates a method making it possible to reduce pollutant emissions at the source and the optimisation of depollution of a diesel engine by modifying the injection, combustion and post-treatment parameters as a function of the content of biofuel present in the fuel.

Adding compounds of agricultural origin of the ester type for example in commercial fuel minimises global emissions of greenhouse gas, but also affects polluting emissions, more particularly emissions of nitrogen oxide (NOx) and particles. Numerous studies such as "A Comprehensive Analysis of Biodiesel Impacts on Exhaust Emissions" (United States Environmental Protection Agency, Air and Radiation EPA420-P-02-001, October 2002) showed that adding ester in fuel impacts polluting emissions by a constant adjustment engine. This can be explained by the significant chemical difference between hydrocarbon molecules composing the fossil fuel and oxygen compounds of the ester family for example.

Biofuels are integrated in gasoil in many countries and the percentage of biofuel in gasoil is highly variable. Political directives exist which are extremely different from one country to another, but recommend the content of biofuel present in the fuel. On the other hand, refining constraints exist which are imposed by commercial specifications limiting the degree of freedom in the integration of biofuel as a function of refining bases composing the fossil fuel.

Numerous methods make it possible to esterify vegetal oil of agricultural origin with a view to synthesising products which can be integrated into the fuel. In addition, vegetal oils have extremely varying origins like rapeseed, palm, soya and other vegetables. These future methods will make it possible to increase the diversity of biofuels using biomass and grease of animal origin, for example. The diversity of the sources and the esterification methods entails significant differences in the chemical structures such as the number of carbon atoms composing the hydrocarbon chains on the one hand, and the ester chemical group on the other hand. These significant chemical specificities entail significant differences as regards the emissions of nitrogen oxide and particles upon their combustion.

The diversity of esterification methods combined with the multiple sources of raw materials, refining and quality constraints and with various recommendations and issues from governments imply that the fuel dedicated to marketed diesel engines have an increasing variability more particularly as regards the content and/or the type of incorporated biofuel. The current engines must be able to operate and emit a quantity of pollutants lower than the prevailing standards in a range of variability of distributed fuels containing a variable proportion and type of biofuel. Therefore, this constraint is taken into account as from the design of the engine and security measures are taken at the level of the engine control. The engine is not adjusted to the optimum for all fuels, but injection and combustion adjustment compromises are made so that the operation of the engine is ensured whatever the rate and/or type of biofuel integrated in the fuel.

Efforts are made as regards post-treatment, more particularly as regards the additive particle filter and the nitrogen oxide transformation systems (DeNOx).

For the correct operation of the additive particle filter, a constant content in additive in the fuel is regulated; for each filling of the fuel tank, the quantity of additive to be injected is determined as a function of the volume of fuel introduced into the tank. To have the particle filter operate whatever the content and the type of biofuel present in the fuel, a safety margin is taken in the injection of the additive and this injection is not optimised as a function of the content and the type of biofuel present in the fuel.

The systems for the post-treatment of nitrogen oxides (NOx) use a reagent and a catalyst. The currently most widely used method implies, as a reagent, a solution of urea making it possible to release ammonia converting the nitrogen monoxide into nitrogen according to the following equation:

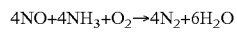

$$4NO+4NH_3+O_2 \rightarrow 4N_2+6H_2O$$

This method must be finely controlled, on the one hand so as to inject sufficient reagent to provide the conversion of nitrogen oxides and on the other hand prevent the injection of excessive additive which would entail a release of ammonia into the atmosphere, which would affect the environment. For this purpose, the DeNOx method includes a sensor measuring the concentration in nitrogen oxide downstream of the post-treatment system. This sensor manages the regulation in post-control.

The variability in the content and type of the biofuel present in the fuel and the impacts thereof on the particle emissions and NOx emissions are then understood today through:

A sufficient content of additive in gasoil to provide the correct operation of the additive particles filter whatever the fuel and the content and type of biofuel.

A post-control based on the NOx sensor positioned downstream of the post-treatment to inject the correct quantity of reagent to provide the transformation of nitrogen oxide.

The non optimised addition, as a function of the content and type of biofuel present in the fuel, of the additives used for the post-treatment of particles by the additive particle filters induces either an excessive dimensioning of the additive tank or a more frequent filling in this tank. The overall constraints aboard the vehicle limit the volume available to the additive tank. On the other hand, manufacturers wish the intervals in kilometers between two fillings of the additive tank to be as great as possible and not at the driver's costs. The utilisation of additives in excess does not meet the overall nor interval constraints between two fillings.

The post-control of the DeNOX system based on the NOx sensor, positioned downstream of the post-treatment, is a reactive control but not a preventive one, as a matter of fact the regulation increases the rate of reagent if the sensor detects a concentration in NOx greater than the target value and reversely limits the rate of reagent when the sensor detects an NOx concentration lower than the target value. The amplitude of the oscillations about the target value and the time required for the regulation to reach this target value can be affected by the content and the type of biofuel present in the fuel; this entails a temporary increase in polluting emissions.

The additive particle filter becomes a predominant solution for the depollution of diesel vehicles as from the beginning of the years 2000 and the DeNOX systems using the AdBlue reagent for example are more and more present on diesel vehicles since 2004.

The anti-pollution standards are always stricter and the vehicle and engine manufacturers must always reduce the regulatory emissions in the exhaust gas such as nitrogen oxide and the particles, for each vehicle or engine sold, in the whole life cycle thereof and while providing a minimum additional cost.

A need exists for improving the management of injection, combustion and post-treatment of diesel engines by taking into account the content and/or the type of biofuel in fuel.

The document US2004000275 deals with a fuel injection system feeding the vehicle with the capacity of estimating the fuel in its own system, which makes it possible to improve the injection parameters. The system is limited to the improvement of injection parameters adjustments and is oriented towards the treatment of fuels for controlled ignition engines. Besides, this document does not disclose the aboard method for measuring the quality of the fuel.

The document WO 94/08226 deals with an aboard method for determining, by near infrared spectroscopy of the proprieties of the fuel. This method does not include the determination of the biofuel rate in the fuel feeding a diesel engine and provides no action aiming neither at minimising the pollutants at the source nor at optimising the engine post-treatment parameters.

The document "Fluid condition monitoring sensors for diesel engine control" discloses an aboard system making it possible to know the rate of FAME (Fatty Methyl Ester) in gasoil. The near infrared technology has the main drawback of the low life duration of the light source which only partially meets the robustness requirements imposed by the automobile, for example. Besides, this method requires a single application sensor exclusively making it possible to measure the rate of biofuel in the diesel or the rate of ethanol in the gasoline thus implying a specific additional cost to meet a unique problem.

The document WO 02095376 makes it possible to check the engine operation mode as a function of the analysis of exhaust gas. Such method implements a sensor on the exhaust line which must meet the strength constraints of the automobile market, for example, and this in a particularly difficult environment (acidity of gas for example); this induces a significant extra cost. On the other hand, the control of the engine parameters as a function of the analysis of emission gases is, by definition, a reagent control and a posteriori inducing the presence of emissions, more particularly with transient speed.

The document WO2006100377 discloses the optimisation of a combustion engine implementing the measurement of the molecule structure of the fuel using a near infrared device. The present invention does not require taking into account such a molecular structure detail, but is concerned with the characterisation of chemical functions, chemical compound families and recognition of molecule groups making it possible to know the rate and the type of biofuel present in the fuel.

The invention aims at meeting the need for determination of the content and type of biofuel present in the fuel adapted to the fuel/polluting emissions couple by providing a method for pre-positioning injection, combustion and post-treatment parameters based on the content and type of biofuel present in the fuel.

For this purpose, The invention makes it possible to pre-position, on the one hand injection and combustion parameters so as to minimise the polluting emissions at the source, as a function of the content and type of biofuel of the fuel, and on the other hand optimise the post-treatment parameters so as to minimise the polluting emissions at the outlet of the vehicle while providing a better management of catalysts, additives and post-treatment reagents.

The method according to the invention is adapted to any type of biofuels (methyl- or ethyl ester of rapeseed, palm, sunflower and others, as well as second generation biofuels and future biofuels).

Such a method includes:
- a step of determining the content of biofuel present in the fuel, and/or
- a step of determining the type of biofuel present in the fuel,
- a step of modifying the injection adjustments (for example injection advance, number of injections, duration of injection, introduction rate of the fuel, management of the supercharging: rate, pressure and temperature of the air admitted, variation of the section of the nozzle guide vane of the turbine in the case of a variable geometry turbine) as a function of the content and the type of the biofuel present in the fuel,
- a step of modifying combustion adjustments (for example: rate of exhaust gas re-circulation (EGR), the cooling of EGR, compression ratio in the case of an engine at a variable compression rate, adjustment of the supercharging such as rate, pressure and temperature of air admitted) as a function of the content and/or type of biofuel present in the fuel.
- a step of modifying the adjustment of post-treatment (for example quantity of reagent injected for the DeNOx treatment, quantity of additive injected for a particle treatment using additive particle filter, quantity of added oxygen for the post-oxidation of soot), as a function of the content and/or type of biofuel present in the fuel.
- a step of storing information relative to the content and/or type of biofuel present in the fuel.

This method is applied at a predefined frequency and/or upon occurrence of an event. This method is applied at least upon each tank filling, with the starting of the method being oriented by a positive variation of the level of fuel indicated by the fuel gauge.

The implementation of the method previously implies calibration of laws, parameters and injection mapping, combustion and post-treatment mapping. This calibration makes it possible to define distinct strategies for the engine control in order to take the content and/or the type of biofuel of the fuel into account.

Thanks to the storage of the information relative to the content and/or type of molecule in the fuel, such a method makes it possible to minimise the polluting emissions upon a cold start by optimising the injection, combustion and post-treatment parameters and taking into account the last information stored regarding the content and/or the type of biofuel present in the fuel.

Such a method makes it possible to reconcile the information resulting from the determination of the rate and type of biofuel present in the fuel according to our invention with other existing sensors (more particularly, the NOx sensors positioned downstream of the post-treatment station) with the aim of confirming the correct operation of such sensors or if need be, informing the OBD (On Board Diagnostic) of the failure of one or several of these sensors.

According to a particular embodiment, the content and/or type of biofuel present in the fuel is determined using a sensor. The sensor is positioned on a fuel circuit including the filling system, the fuel tank, the pump gauge module, the fuel filter or filters, the engine feeding circuit and the return circuit to the tank.

According to a particular embodiment, the sensor enables to determine the content and/or type of biofuel present in the fuel, which are based on a spectroscopic analysis using a near infrared technology. As a matter of fact, the near infrared analysis is more particularly well adapted to the qualitative diagnostic of the fuels as far as the near infrared analysis is a highly sensitive method and the near infrared spectrum can be considered as the product "DNA". In addition, the near infrared analysis can easily be reproduced.

In addition, the near infrared technology makes it possible to use a spectrometer without any mobile part of the scattering type, Fourier's transform, light emitting diodes and other devices. Such technologies can be miniaturised. The emission and detection systems can be connected to each other through an optical fibre. Thus, the near infrared technology has the advantage of being easily integrated aboard a vehicle, and is very strong, which implies low costs.

Reference documents for the near infrared can be cited such as the one by L. G. WEYER published in 1985 or the "Handbook of near infrared analysis" published in 1992 or more specific publications such as the spectroscopic applications in petrochemical or refining, as shown in the other articles by Jerome WORKMAN Jr. in 1996 or by M. VALLEUR in 1999.

The information contained in the near infrared spectrum of the fuel is extracted by a mathematical process making it possible to determine the content and/or type of biofuel present in the fuel. This determination of the content and/or type of fuel is taken into account for optimising the injection, combustion and post-treatment adjustments with a view to minimising the polluting emissions of this engine.

According to a particular embodiment, the rate and/or the type of biofuel are calculated from the determination of the molecular structure of the product. As a matter of fact, the molecular structure of the product supplies an extremely fine detail level, making it possible to precisely understand the specificities of the biofuel such as chemical groups or chemical families, for example by evidencing the ester group through the analysis of the molecular structure.

Other objects and advantages of the invention will appear while reading the following description and referring to the appended drawings.

Figure 1:
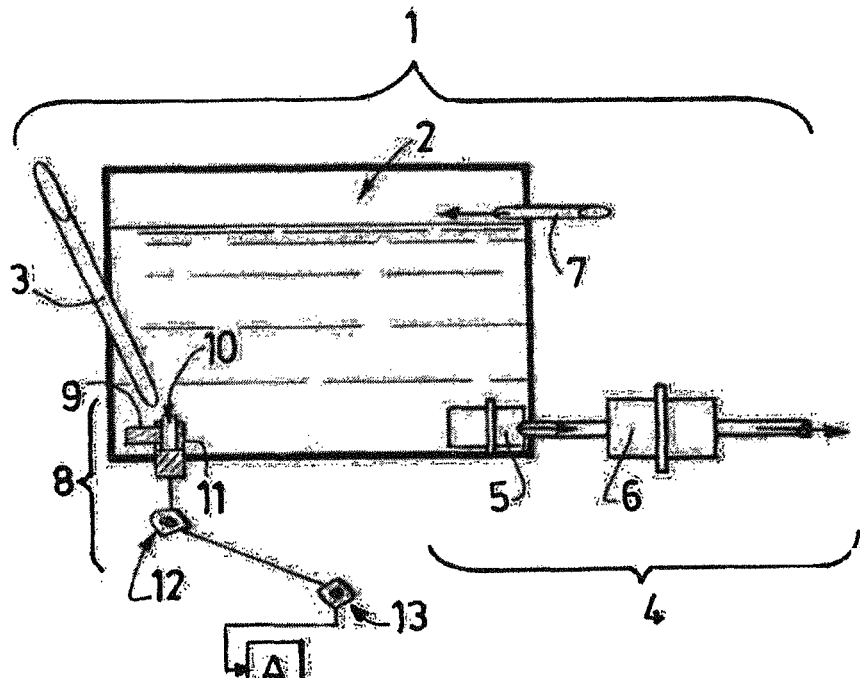
FIG. 1 is a schematic representation of the fuel feeding circuit in an engine wherein the method according to the invention is implemented with an exemplary embodiment of the sensor.

While referring to FIG. 1, a method for minimising the polluting emissions of a vehicle provided with a thermal engine taking into account the content and/or type of biofuel present in the fuel when adjusting injection, combustion and post treatment is disclosed.

The engine is supplied with fuel by the fuel circuit (1) including a fuel tank (2), a fuel tank filling system (3) and a fuel supply circuit (4). The circuit includes for example one or several fuel pumps (5), one or several fuel filters (6) and the return circuit to the tank (7).

According to an embodiment shown in FIG. 1, a spectroscopic sensor (8) is placed out in the fuel circuit (1) and is connected to the electronic or digital system (13) enabling to use the content and/or type of the biofuel present in the fuel when managing the injection, combustion and post-treatment parameters.

In the case of a near infrared analysis, the sensor is composed of a light source (9), a light separation system, a fuel sampling cell (10), a photosensitive detection system (11) and a dedicated calculator (12). It is possible to displace the system for sampling the other components of the spectrometer through optical fibres. The dedicated calculator (12) makes it possible to manage the measuring sequences, to adjust and control the correct operation of the sensor (8). The calculator (12) contains the mathematic models making it possible to carry out all the calculations associated with the treatment of the near infrared spectrum, enabling the auto-diagnosis of the measuring system and the determination of the content and the type of biofuel present in the fuel. The calculator (12) is connected to an electronic or digital system (13) allowing the utilisation of information relative to the content and/or type of biofuel through the engine control for the injection, combustion and post-treatment. This electronic or digital system controls the regulation actuators (A). The functions carried out by the calculator (12) can be ensured and directly executed by the electronic or numerical system (13).

In the near infrared, the sensor (8) can include only one source and only one detector or several light sources as a whole detector or only one source and several detectors. It can use, more particularly in the case of the near infrared, interferential filters, Bragg arrays, dispersive networks, liquid crystals, Fourier's transform systems or a linear camera for separating light. The microanalyser (8) can have sequential or multiplex access.

The sensor (8) can be a near infrared bar spectrometer composed of several hundreds of photodiodes which record each the light intensity at a given wavelength. The detector which is inside the sensor (8) is a highly sensitive semiconductor based on silicon (Si) or an alloy of a complex type (InGaAs, InAs, InSb, PbS, PbSe) or a CMOS or CCD type component. The detector can be cooled or not.

Figure 2:
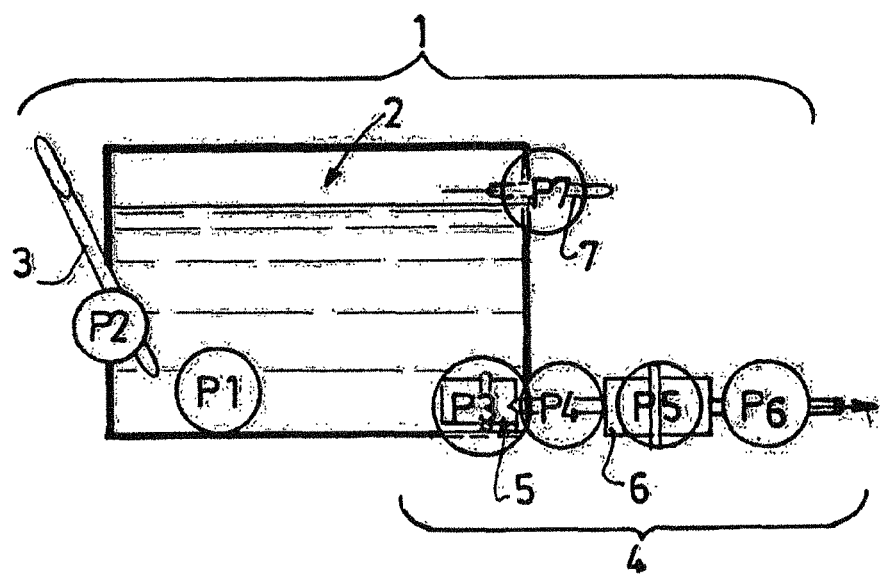
FIG. 2 is a diagrammatic representation of a fuel feeding circuit in an engine indicating the possible locations of the sensor.

The sensor (8) may be positioned in the tank (position P1 in FIG. 2) at the level of the fuel tank filling system (position P2 in FIG. 2), in the pump gauge module (position P3 in FIG. 2), in the fuel supply circuit of the engine. In the later case, the sensor (8) may be positioned between the pump (5) and the filter (6) (position P4 in FIG. 2), in the fuel filter (position P5 in FIG. 2) or downstream of the fuel filter (position P6 in FIG. 2). The sensor can also be positioned in the fuel return circuit (position P7 in FIG. 2).

The sensor (8) is so arranged as to make measurements in the spectrum regions between 780 and 2,500 nanometers (12,820 cm$^{-1}$ to 4,000 cm$^{-1}$). For example, successive measuring ranges must be provided between 780 nanometers and 1,100 nanometers (12,820 cm$^{-1}$ to 9,090 cm$^{-1}$), 1,100 nanometers and 2,000 nanometers (9,090 cm$^{-1}$ to 5,000 cm$^{-1}$) and 2,000 nanometers and 2,500 nanometers (5,000 cm$^{-1}$ to 4,000 cm$^{-1}$). For this purpose, the sampling system is so arranged as to show an optical path, which means a product thickness through which measurement is made between 0.5 millimeters and 100 millimeters, i.e. optical paths corresponding to the wavelength ranges of 50 millimeters to 100 millimeters in the first case, 10 millimeters to 20 millimeters in the second case and 0.5 millimeters to 5 millimeters in the last case.

The sensor (8) is so arranged as to carry out the near infrared spectrum of the fuel circulating in the fuel circuit feeding the engine in reflectance, transmittance or absorbance.

The sensor (8) has a spectral resolution (accuracy) which is adjustable from 1 cm$^{-1}$ to 20 cm$^{-1}$, preferentially at 4 cm$^{-1}$.

The optical system and sensor sampling system (8) can also be self-cleaning which makes it possible to prevent disassembling it to clean it.

The measurements of near infrared spectra of the fuel are carried for example in absorbance in the considered wavelength areas. The absorbance values measured for each selected wavelength are introduced into universal mathematic and statistic models previously calibrated on a reference data bank, according to the known rules of chemometry, in order to supply information to the multiple entry matrix, making it possible to determine the content and type of biofuel present in the fuel.

This information on quality is supplied to the engine control which modifies, as a function of such content and type of biofuel, the injection, combustion and post-treatment adjustment (parameters, laws and maps) so as to optimise the adjustments with a view to minimising the polluting emissions by the engine.

The best parameters, laws and/or maps for the injection, combustion and post-treatment of the engine are selected by the electronic or digital system as a function of the Usual information collected by the various sensors and detectors and also by the sensor 8 which now informs it on the content and/or type of the biofuel present in the fuel.

The parameters, laws and maps of the engine can be selected to minimise or limit the emissions in the exhaust gases for the iso performances of the engine or for increasing the performances of the engine with iso emissions.

The determinations of the content and type of biofuel present in the fuel can be carried out by the sensor 8 regularly over time.

According to a particular embodiment, a detector of the volume of fuel present in the tank 2 can also be provided. The starting of the measurement by the sensor 8 is then controlled to occur every time the tank fuel is filled (increase in the volume in the fuel tank).

A step of storing information relative to the content and/or type of biofuel is used so as to make a history of such content and such type of biofuel. Upon starting the engine, the last content and the last type of biofuel stored are used for the engine control, in order to adjust the parameters, laws and map for the injection, combustion and post-treatment, as a function of the content and type of biofuel.

The method according to the invention includes an auto-diagnostic system making it possible to check the correct operation of the sensor 8. In case of failure on the sensor 8, the auto-diagnostic system detects the trouble and informs the digital or electronic system in charge of the engine control about said trouble. Under such circumstances, this electronic or digital system takes the following action:

The system assumes that the content and/or type of biofuel present in the fuel are the most unfavourable and accordingly adjust the parameters, laws and maps for the injection, combustion and post-treatment, so as to minimise the polluting emissions at the expense of performances.

The system informs the OBD ("On Board Diagnostic") of the failure of the sensor 8.

Figure 3:
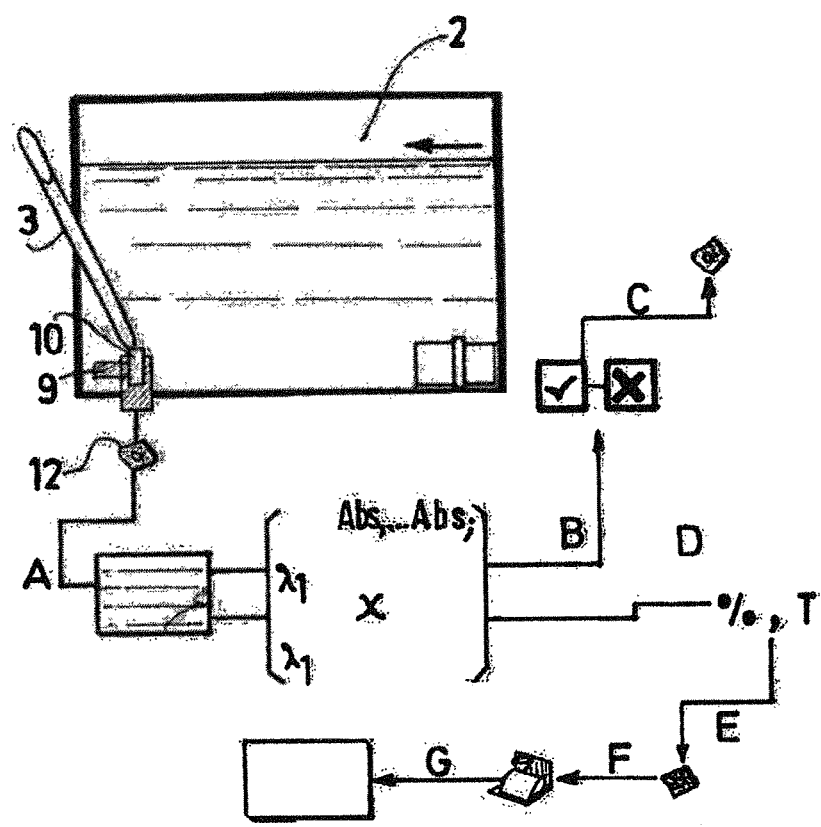
FIG. 3 is a diagram showing the steps of the method and more particularly the steps of determining the content and/or the type of biofuel present in the fuel and the steps of adjusting the engine for minimising the polluting emissions.

The system informs the user of the engine or the company in charge of the maintenance thereof of the failure of the sensor 8, FIG. 3 shows the various steps of the method:

step A: collection of the near infrared spectrum of the fuel step B: auto-diagnostic of the sensor applied to the near infrared spectrum step C: communication of the status of the determination of the content and/or type of the biofuel to the diagnostic centralised system (On Board Diagnostic)

step D: determination of the content and/or the type of biofuel present in the fuel from the mathematic processing applied to the near infrared spectrum of the fuel step E: in case the sensor is valid, transfer of the information relative to the content and/or the type of biofuel to the digital or electronic system in charge of the engine control step F: selection or modification of the parameters, laws and/or maps adapted by the digital or electronic system in charge of the engine control;

step G: adjustment of the engine as a function of the adapted parameters, laws and/or maps.

The invention claimed is:

1. A method for adjusting injection, combustion and/or post-treatment parameters of an internal combustion engine with auto-ignition including:

determining the content and type of biofuel present in the fuel feeding the injection system using a spectroscopic sensor to measure values of near infrared spectra of the fuel and by introducing the measured values into universal mathematic and statistic models to extract information relative to the content and/or type of biofuel present in the fuel; and storing this information and recording in a memory a history of the determined content and of biofuel.

2. A method according to claim 1, characterised in that it includes a step of adjusting the rate of injection of post-treatment reagents and/or additives as a function of the content and/or the type of biofuel present in the fuel feeding the engine.

3. A method according to claim 1, characterised in that it includes a step of adjusting at least one of the injection parameters such as the injection advance, the number of injection, the duration of injection, the rate of introduction of the fuel, the management of supercharging, such as the rate, pressure and temperature of the admitted air, the variation in the section of the turbine nozzle guide vane in the case of a variable geometry turbine as a function of the content and/or the type of biofuel present in the fuel feeding the engine.

4. A method according to claim 1, characterised in that it includes the step of adjusting at least one of the combustion parameters such as the rate of exhaust gas re-circulation (EGR), the cooling of re-circulated exhaust gas, the compression ratio in the case of an engine at a variable compression rate and the opening and dosing of valve as a function of the content and/or the type of biofuel present in the fuel feeding the engine in order to minimize pollutant emissions at the source thereof.

5. A method according to claim 1, characterised in that the last information stored are used again for pre-positioning the injection, combustion and post-treatment parameters in order to minimize the pollutant emissions upon the starting of the vehicle.

6. A method according to claim 1, characterised in that said step of determining the content and/or the type of biofuel present in the fuel and the pre-positioning and the optimization of the injection, combustion and post-treatment parameters are carried out periodically and/or upon the order of the digital or electric system (13) in charge of managing the engine control and/or as soon as a new filling of the fuel tank (2) is executed.

7. A method according to claim 1, characterised in that the content and/or the type of biofuel present in the fuel are determined from a near infrared sensor (8) positioned on a fuel circuit including a fuel tank filling system, a fuel tank (2), a pump gauge module, fuel filter or filters (6), an engine fuel feeding circuit and a return circuit to the fuel tank.

8. A method according to claim 7, characterised in that the sensor (8) is self-cleaning.

9. A method according to claim 7, characterised in that the step of determining the content and the type of the biofuel present in the fuel includes an auto-diagnosis of the validity of the sensor (8) and the determined content and/or type of biofuel.

10. A method according to claim 7, characterised in that, when a malfunction of the sensor or an erroneous determination of the content or type of biofuel is diagnosed, an engine control management system takes into account the content and type of biofuel present in the fuel which are the most unfavorable and securely adjusts the injection combustion and post-treatment parameters so as to minimize the risk of pollutant emissions at the expense of engine performances.

11. A method according to claim 7, characterised in that the information resulting from the determination of the content and/or type of biofuel present in the fuel are reconciled and compared with information from other existing sensors with a view to confirming the correct operation of the assembly of sensors or if need be informing an OBD (On Board Diagnostic) of the failure of one or several of these sensors.

12. A method according to anyone of claims 1, 9 or 10 characterised in that, when a malfunction of one or several sensors is noted, the user of a vehicle is informed by a visual or a sound warning.

13. A method according to anyone of claims 1, 9 or 10, characterised in that, when a malfunction of one or several sensors is noted, the company in charge of the vehicle maintenance is informed through a wireless communication.

14. Equipment for implementing the method according to claim 1, comprising:
    a spectroscopic sensor positioned on the fuel circuit; and
    a calculator for determining the content of biofuel present in the fuel.

15. Equipment according to claim 14, characterised in that the spectroscopic sensor is a near infrared sensor.

16. A motorization system including:
    an internal combustion engine with auto-ignition;
    a fuel tank;
    a pump gauge module;
    at least one fuel filter;
    an engine fuel supply circuit and a return circuit to the fuel tank; and
    a close-infrared spectroscopic sensor positioned on the fuel circuit for determining the content and type of biofuel present in the fuel.

* * * * *